United States Patent
Lee et al.

(10) Patent No.: US 10,219,785 B2
(45) Date of Patent: Mar. 5, 2019

(54) METHOD, APPARATUS, AND HIGH INTENSITY FOCUSED ULTRASOUND (HIFU) SYSTEM FOR GENERATING ULTRASOUND THAT FORMS MULTI-FOCI VIA MEDICAL IMAGE IN REGION OF INTEREST

(71) Applicant: SAMSUNG ELECTRONICS CO., LTD., Suwon-si (KR)

(72) Inventors: Ho-taik Lee, Yongin-si (KR); Won-chul Bang, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1422 days.

(21) Appl. No.: 14/180,476

(22) Filed: Feb. 14, 2014

(65) Prior Publication Data

US 2014/0236061 A1     Aug. 21, 2014

(30) Foreign Application Priority Data

Feb. 15, 2013    (KR) .................. 10-2013-0016603

(51) Int. Cl.
*A61B 8/00*   (2006.01)
*A61B 8/08*   (2006.01)
(Continued)

(52) U.S. Cl.
CPC .............. *A61B 8/48* (2013.01); *A61B 8/5261* (2013.01); *A61N 7/02* (2013.01); *A61B 6/032* (2013.01);
(Continued)

(58) Field of Classification Search
CPC ........... A61B 6/032; A61B 8/085; A61B 8/48; A61B 8/5261; A61N 2007/027; A61N 7/02
See application file for complete search history.

(56) References Cited

U.S. PATENT DOCUMENTS 5,678,554 A    10/1997   Hossack et al.
5,817,020 A *  10/1998   Ishii ..................... A61B 8/0875
                                                    600/437
(Continued)

FOREIGN PATENT DOCUMENTS

JP    2010-68884 A    4/2010
JP    2012-5602 A     1/2012
(Continued)

OTHER PUBLICATIONS

Ebbini, Emad S., et al., "A Spherical-Section Ultrasound Phased Array Applicator for Deep Localized Hyperthermia," IEEE, Transactions on Biomedical Engineering, vol. 38, No. 7, Jul. 1991; pp. 634-643.
(Continued)

*Primary Examiner* — Amelie R Gillman
(74) *Attorney, Agent, or Firm* — Sughrue Mion, PLLC

(57) ABSTRACT

A method of generating therapeutic ultrasound that forms multi-foci by a therapeutic ultrasound probe, the method including: obtaining a medical image including anatomical information of a region of interest in a subject; calculating, by using the medical image, characteristics which influence traveling of therapeutic ultrasound with respect to tissues included in the region of interest; calculating, by using the calculated characteristics, a parameter of the therapeutic ultrasound for forming multi-foci in the region of interest; and generating the therapeutic ultrasound according to the calculated parameter.

17 Claims, 9 Drawing Sheets

(51) Int. Cl.
  *A61N 7/02* (2006.01)
  *A61B 6/03* (2006.01)
(52) U.S. Cl.
  CPC ......... *A61B 8/085* (2013.01); *A61N 2007/027* (2013.01)

(56) References Cited

U.S. PATENT DOCUMENTS

| | | | | |
|---|---|---|---|---|
| 2004/0122323 | A1* | 6/2004 | Vortman | A61N 7/02 600/459 |
| 2010/0030076 | A1* | 2/2010 | Vortman | A61N 7/02 600/439 |
| 2011/0295105 | A1* | 12/2011 | Konofagou | A61M 37/0092 600/411 |
| 2013/0237822 | A1* | 9/2013 | Gross | A61B 8/13 600/439 |

FOREIGN PATENT DOCUMENTS

| | | |
|---|---|---|
| KR | 10-1028805 B1 | 4/2011 |
| KR | 10-1118480 B1 | 3/2012 |

OTHER PUBLICATIONS

Fink, Mathias, "Time Reversal of Ultrasonic Fields—Part I: Basic Principles," IEEE, Transactions on Ultrasonics, Ferroelectrics, and Frequency Control, vol. 39, No. 5, Sep. 1992; pp. 555-566.

\* cited by examiner

FIG. 5

| material | CT number (HU) | density (kg/m³) | speed of sound (m/s) | Attenuation (dB/(MHz·cm)) | Acoustic Impedance (kg/m²/sec)× 10⁶ |
|---|---|---|---|---|---|
| water (25°C) | 0 | 988 | 1497 | 0.0022 | 1.50 |
| Fat | -100~-50 | 950 | 1440-1490 | 0.48 | 1.38 |
| liver | 40~60 | 1060 | 1547-1585 | 0.5 | 1.65 |
| Kidney | 30 | 1040 | 1557 | 1.0 | 1.62 |
| Brain | 37 | 1030 | 1550 | 0.6 | 1.55 |
| Heart | 55 | 1045 | 1570 | 0.52 | |
| blood | 40 | 1025 | 1570 | 0.2 | 1.61 |
| muscle | 10~40 | 1070 | 1542-1626 | 1.09 | 1.70 |
| Skin* | 75 | 1090 | 1730 | 0.8~3.6 | 1.7 |
| Bone | 1000 | 1912 | 4080 | 6.9~9.94 | 7.8 |

METHOD, APPARATUS, AND HIGH INTENSITY FOCUSED ULTRASOUND (HIFU) SYSTEM FOR GENERATING ULTRASOUND THAT FORMS MULTI-FOCI VIA MEDICAL IMAGE IN REGION OF INTEREST

CROSS-REFERENCE TO RELATED APPLICATIONS

This application claims priority from and the benefit of Korean Patent Application No. 10-2013-0016603, filed on Feb. 15, 2013, in the Korean Intellectual Property Office, the disclosure of which is incorporated herein for all purposes in its entirety by reference.

BACKGROUND

1. Field

Exemplary embodiments of the present disclosure relate to methods, apparatuses, and high intensity focused ultrasound (HIFU) systems for generating ultrasound that forms multi-foci in a region of interest.

2. Description of the Related Art

Along with the technological advancements in medical areas, techniques for the local treatment of tumors have been developed from minimal-invasive surgery to non-invasive surgery. An example of a recently developed non-invasive surgery method is a high-intensity focused ultrasound (HIFU) treatment method which is widely used as it is harmless to the human body. In a HIFU treatment method, high intensity ultrasound is focused and irradiated on a lesion inside a human body to necrose a lesion tissue. The focused ultrasound that is irradiated on the lesion is converted into thermal energy to increase a temperature of the irradiated portion so as to cause coagulative necrosis in the lesion tissue and blood vessels therein. As the temperature of the lesion onto which the ultrasound is irradiated increases instantaneously, just the irradiated lesion may be effectively removed while preventing diffusion of heat to peripheral portions adjacent to the irradiated lesion.

A HIFU treatment device includes a transducer (or an ultrasound treatment probe) that converts an electrical signal to ultrasound. A position where an ultrasound focus is to be formed may be controlled by adjusting a particle velocity of the transducer. Recently, a method of simultaneously forming a plurality of foci (i.e., multi-foci) by using a transducer including a plurality of elements (or ultrasound treatment probes) has been developed. The above information disclosed in this Background section is only for enhancement of understanding of the background of the invention and therefore it may contain information that does not form any part of the prior art.

SUMMARY

Exemplary embodiments of the present invention provide methods, apparatuses, and high intensity focused ultrasound (HIFU) systems for generating ultrasound that forms multi-foci in a region of interest.

Additional aspects will be set forth in part in the description which follows and, in part, will be apparent from the description, or may be learned by practice of the presented embodiments.

According to an aspect of the present invention, a method of generating therapeutic ultrasound that forms multi-foci by a therapeutic ultrasound probe, includes: obtaining a medical image including anatomical information of a region of interest in a body; calculating, by using the medical image, characteristics of tissues included in the region of interest which influence traveling of the therapeutic ultrasound; calculating, by using the calculated characteristics, a parameter of the therapeutic ultrasound for forming multi-foci in the region of interest; and generating the therapeutic ultrasound according to the calculated parameter.

According to another aspect of the present invention, a non-transitory computer readable recording medium having embodied thereon a program for executing the method described above is disclosed.

According to another aspect of the present invention, a therapeutic ultrasound probe for generating therapeutic ultrasound that forms multi-foci may include: a tissue characteristic calculating unit that calculates, by using a medical image including anatomical information of the region of interest, characteristics of tissues included in a region of interest which influence traveling of the therapeutic ultrasound; a parameter calculating unit that calculates, by using the calculated characteristics, a parameter of the therapeutic ultrasound for forming multi-foci in the region of interest; and a ultrasound generating unit that generates the therapeutic ultrasound according to the calculated parameter.

BRIEF DESCRIPTION OF THE DRAWINGS

These and/or other aspects will become apparent and more readily appreciated from the following description of the embodiments, taken in conjunction with the accompanying drawings of which:

FIG. 5 illustrates a model generated by using a second model generating unit according to an embodiment of the present invention;

DETAILED DESCRIPTION

Figure 1:
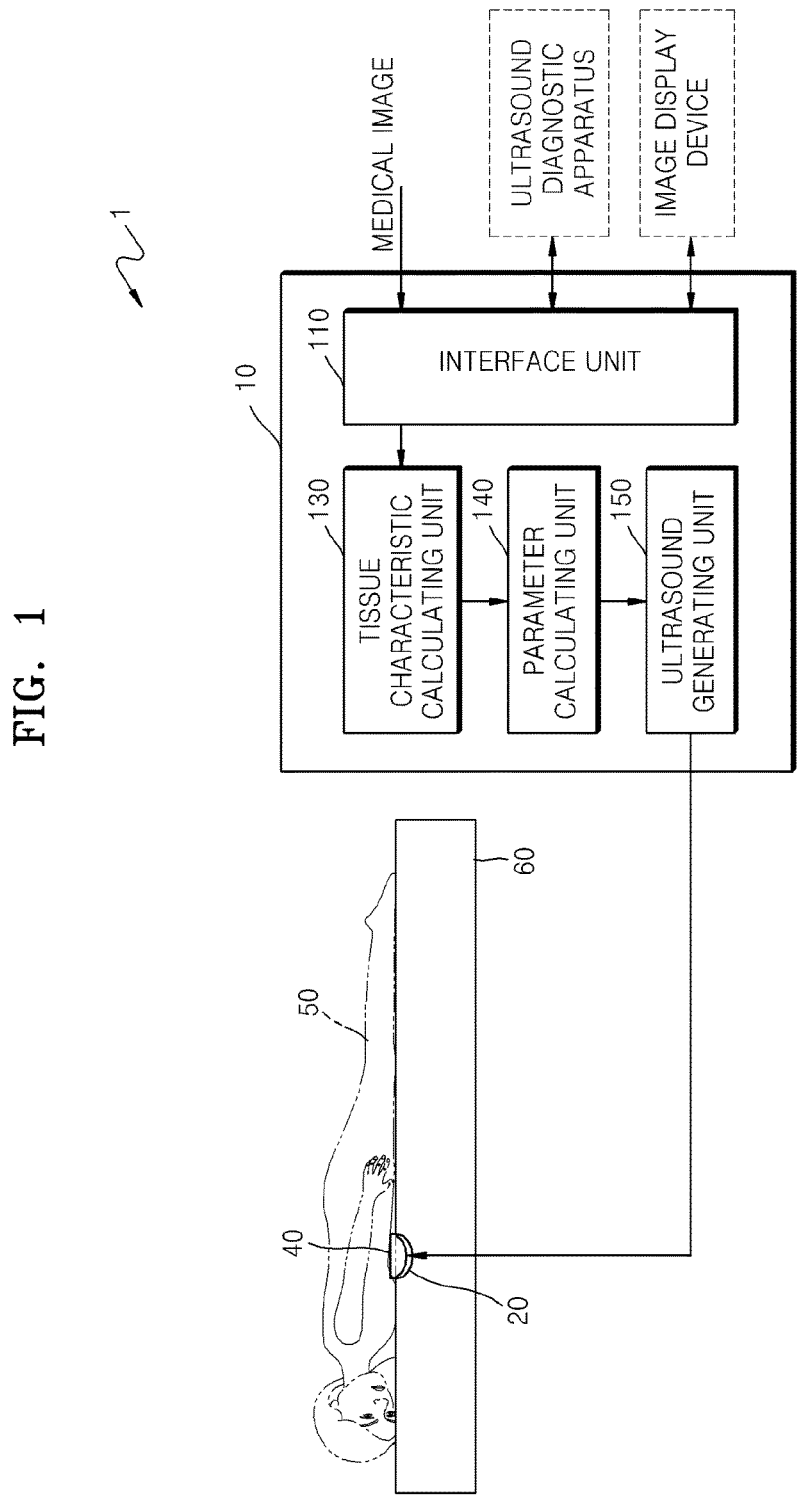
FIG. 1 illustrates a high intensity focused ultrasound (HIFU) system according to an embodiment of the present invention.

Reference will now be made in detail to embodiments, examples of which are illustrated in the accompanying drawings, wherein like reference numerals refer to the like elements throughout the application. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list. The aspects of the invention in this application are not limited to the disclosed operations and sequence of operations. For instance, operations may be performed by various elements and components, may be consolidated, may be omitted, and may be altered without departing from the spirit and scope of the present invention. Although some features may be described with respect to individual exemplary embodiments, aspects need not be limited thereto such that features from one or more exemplary embodiments may be combinable with other features from one or more exemplary embodiments.

FIG. 1 illustrates a high intensity focused ultrasound (HIFU) system 1 according to an embodiment of the present invention.

Referring to FIG. 1, the HIFU system 1 may include a central workstation 10 and an ultrasound treatment probe 20. Also, the central workstation 10 may include an interface unit 110, a tissue characteristics calculating unit 130, a parameter calculating unit 140, and an ultrasound generating unit 150.

In FIG. 1, only elements of the central workstation 10 related to the current embodiment of the present invention are illustrated. Thus, it would be obvious to one of ordinary skill in the art that other general-use elements may be further included in the central workstation 10.

Also, the interface unit 110, the tissue characteristics calculating unit 130, the parameter calculating unit 140, and the ultrasound generating unit 150 of the central workstation 10 illustrated in FIG. 1 may include one processor or a plurality of processors. A processor may be formed as an array including a plurality of logic gates or as a combination of a general-use microprocessor and a memory device in which a program that is executable in the microprocessor is stored. Also, it would be obvious to one of ordinary skill in the art that other various processors in the form of hardware or other forms may be used.

The ultrasound treatment probe 20 irradiates therapeutic ultrasound to a region of interest in a subject 50. The therapeutic ultrasound may refer to high intensity focused ultrasound (HIFU), but is not limited thereto.

In detail, the ultrasound treatment probe 20 may be installed in a bed 60 on which the subject 50 is lying and may irradiate the therapeutic ultrasound to a region of interest in a body of the subject 50 and remove a lesion included in the region of interest. A gel pad 40 which may be helpful for transmitting the therapeutic ultrasound may be disposed between the subject 50 and the bed 60.

A position where the ultrasound treatment probe 20 is installed is not limited to the bed 60. For example, the ultrasound treatment probe 20 may be installed above the subject 50 and irradiate the therapeutic ultrasound toward the subject 50 located below the ultrasound treatment probe 20.

Figure 2:
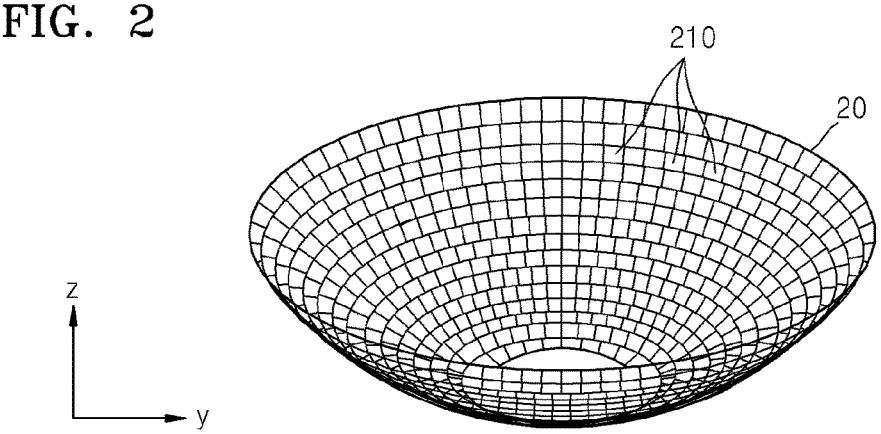
FIG. 2 is a schematic view illustrating an ultrasound treatment probe according to an embodiment of the present invention.

FIG. 2 is a schematic view illustrating an ultrasound treatment probe 20 according to an embodiment of the present invention.

Referring to FIG. 2, the ultrasound treatment probe 20 may have a form of a disk-shaped support substrate having a concave center. At least one element 210 is disposed on the disk-shaped support substrate. When the ultrasound treatment probe 20 is formed of a plurality of elements 210, the elements 210 may receive a signal transmitted by using the central workstation 10 of FIG. 1 to individually irradiate therapeutic ultrasound, and a time to irradiate the ultrasound may also be set differently for each of the elements 210.

As the elements 210 individually irradiate ultrasound, a position where the ultrasound is focused may also vary although the position of the ultrasound treatment probe 20 is fixed. Also, multi-foci may be formed.

In detail, each of the elements 210 may convert an electrical signal having a predetermined amplitude and phase, which is input from the central workstation 10 of FIG. 1, to an ultrasound signal having a predetermined intensity and phase. The elements 210 may be formed of, for example, a piezoelectric transducer.

Ultrasound generated by each of the elements 210 may be focused on a region of interest inside the subject 50 (FIG. 1) that undergoes treatment. The therapeutic ultrasound that is focused on the region of interest may be converted into thermal energy to increase a temperature of the region of interest and to necrose a legion tissue included in the region of interest. The region of interest may be a tissue in the breast, liver, stomach, or the like, but is not limited thereto.

In addition, the ultrasound treatment probe 20 illustrated in FIG. 2 is only an example according to an exemplary embodiment of the invention, and various other types and examples of the ultrasound treatment probe 20 are included in the scope of the present application.

Referring to FIG. 1 again, the central workstation 10 may calculate characteristics which may influence the travelling of the therapeutic ultrasound, in the tissues included in a region of interest, by using a medical image including anatomical information of the region of interest. The central workstation 10 may calculate one or more parameters of the therapeutic ultrasound for forming multi-foci in the region of interest by using the calculated characteristics. In addition, the central workstation 10 may generate therapeutic ultrasound according to the determined parameter.

A medical image may be a computed tomography (CT) image including anatomical information of the region of interest, but is not limited thereto.

Hereinafter, functions of the interface unit 110, the tissue characteristics calculating unit 130, the parameter calculating unit 140, and the ultrasound generating unit 150 of the central workstation 10 will be described in detail.

The interface unit 110 may obtain a medical image including anatomical information of the region of interest. The region of interest may refer to a region where the therapeutic ultrasound irradiated by using the therapeutic ultrasound probe 20 may form multi-foci, and may be a region including a lesion in the subject 50 that needs to be treated. The interface unit 110 may transmit an input medical image to the tissue characteristics calculating unit 130.

The interface unit 110 may include a communication interface unit and a user interface unit. The communication interface unit may receive a medical image from the outside, and transmit information about therapeutic ultrasound to the therapeutic ultrasound probe 20. Also, the interface unit 110 may receive electrical pulse signals from a diagnostic ultrasound probe 70 which will be described later. In addition, the communication interface unit may transmit an ultrasound image generated by using the central workstation 10 to an image display device 30 which will be described later. The user interface unit may receive from a user information about a region of interest or information about positions of multi-foci. For example, the user interface unit may be any of input and output devices such as a display panel, a mouse, a keyboard, a touch screen, a monitor, and a speaker provided in the central workstation 10.

The tissue characteristics calculating unit 130 calculates characteristics which may influence travelling of the therapeutic ultrasound in tissues in the region of interest. The characteristics are calculated by using a medical image. In detail, the tissue characteristics calculating unit 130 calculates, according to a medical image, characteristics of tissues existing on paths along which the therapeutic ultrasound travels from components in the therapeutic ultrasound probe 20 to multi-foci. The characteristics of tissues may include one or more of the following: a speed of the therapeutic ultrasound through each of the tissues, a density of each of the tissues, and an attenuation coefficient of the therapeutic ultrasound in each of the tissues.

The multi-foci refer to a plurality of foci that are formed by focusing the therapeutic ultrasound on the region of interest by using the therapeutic ultrasound probe 20. That is, unlike a single focus which denotes one focus formed by irradiating therapeutic ultrasound one time by using the therapeutic ultrasound probe 20, multi-foci refers to multiple foci formed at the same time by one time irradiation of the therapeutic ultrasound.

Figure 3:
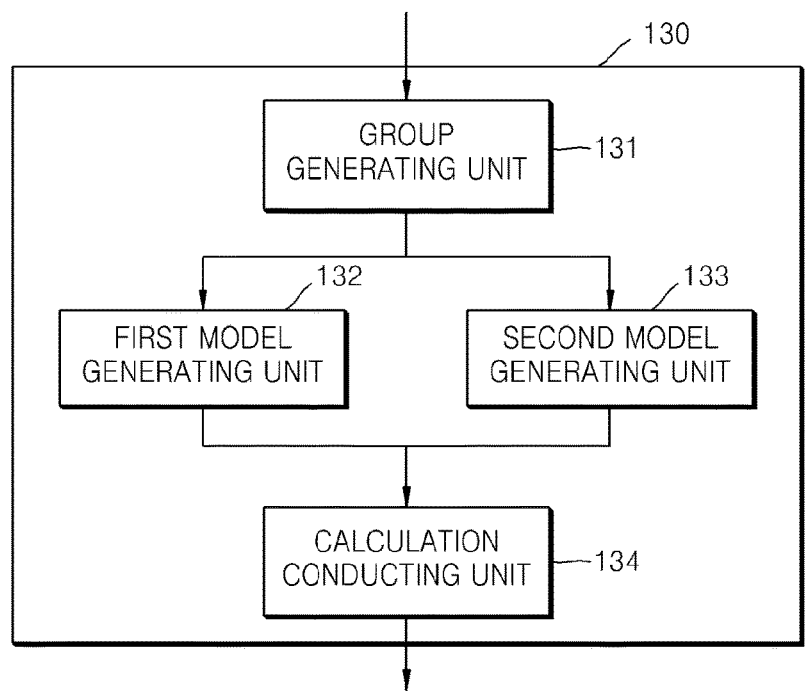
FIG. 3 illustrates a tissue characteristics calculating unit according to an embodiment of the present invention.

FIG. 3 illustrates the tissue characteristics calculating unit 130 according to an embodiment of the present invention.

Referring to FIG. 3, the tissue characteristics calculating unit 130 may include a group generating unit 131, a first model generating unit 132, a second model generating unit 133, and a calculation conducting unit 134. Only elements of the tissue characteristics calculating unit 130 relating to the current embodiment of the present invention are illustrated in FIG. 3. Accordingly, it may be obvious to one of ordinary skill in the art that other general-use elements may be further included in the tissue characteristics calculating unit 130. In addition, the tissue characteristics calculating unit 130 illustrated in FIG. 3 may include one or a plurality of processors.

The group generating unit 131 receives a medical image via the interface unit 110 and identifies from the medical image the type of at least one tissue that exists on a path along which the therapeutic ultrasound travels from the therapeutic ultrasound probe 20 to multi-foci. At least one tissue may be included on the path along which the therapeutic ultrasound travels from the therapeutic ultrasound probe 20 to the multi-foci. For example, the at least one tissue may include the skin, a bone, a muscle, blood, an organ, etc.

The group generating unit 131 groups tissues according to the identified types thereof. For example, if the medical image is a CT image, the group generating unit 131 may group tissues into a first group and a second group in consideration of a CT number of tissue obtained from the medical image.

The first group and the second group grouped by using the group generating unit 131 may be set according to a value of the CT number. In detail, the group generating unit 131 may set tissues whose CT number is in a predetermined range as the first group, and tissues whose CT number is very large or very small, or out of the predetermined range, as the second group.

For example, the CT number of bone is known to be +1000, and the CT number of fat is known to be about −100 to −50. When compared to the CT number of the liver of 40 to 60, the CT number of the kidney of 30, the CT number of the brain of 37, and the CT number of blood of about 40, it may be considered that the CT number of bone is very large, and the CT number of fat is very small. Accordingly, the group generating unit 131 may group those tissues other than the bone and fat as the first group, and the bone and fat as the second group.

As described above, the group generating unit 131 may group tissues into the first group and the second group, and may transmit information about tissues corresponding to the first group and information about tissues corresponding to the second group to the first model generating unit 132 and the second model generating unit 133, respectively.

The first model generating unit 132 may generate a first model indicating characteristics regarding each of the tissues included in the first group by using the CT number corresponding to each of the tissues included in the first group. Here, the characteristics refer to physical characteristics of at least one tissue and may include one or more of the following: a speed of therapeutic ultrasound through each of the tissues, a density of each of the tissues, and an attenuation coefficient of therapeutic ultrasound regarding each of the tissues, but are not limited thereto.

Figure 4:
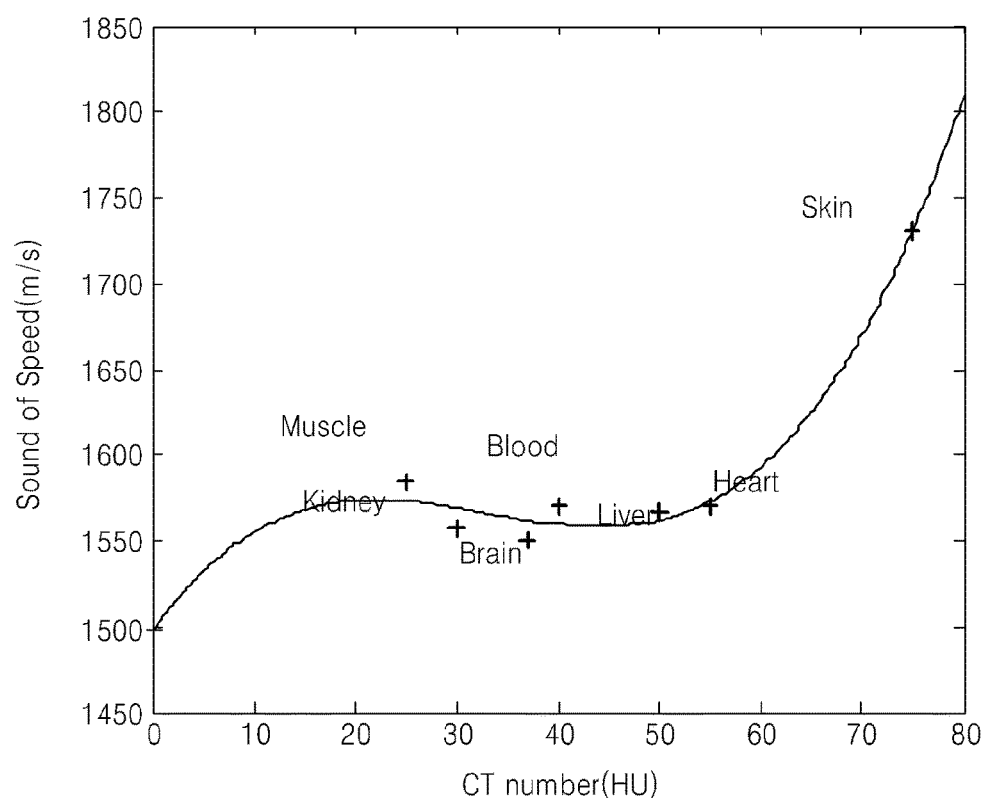
FIG. 4 illustrates a model generated by using a first model generating unit according to an embodiment of the present invention.

FIG. 4 illustrates a model generated by using the first model generating unit 132 (see FIG. 3) according to an embodiment of the present invention.

Referring to FIG. 4, a model generated by using the first model generating unit 132 is illustrated as a graph, but the embodiments of the present invention are not limited thereto. The first model generating unit 132 may calculate a speed of therapeutic ultrasound through each of the tissues according to Equation 1 below.

$$c = 0.0028h^3 - 0.28h^2 + 8.2313h + 1497 \quad \text{[Equation 1]}$$

In Equation 1, c is a speed of therapeutic ultrasound (unit: m/s) through a tissue, and h is a CT number of the tissue (unit: Hounsfield unit (HU)).

The first model generating unit 132 may calculate a speed of the therapeutic ultrasound with respect to tissues of the first group, and approximate the calculated values to generate a graph model of the speed of the therapeutic ultrasound through the tissues included in the first group.

Alternatively, the first model generating unit 132 may generate a model regarding a density of each of the tissues included in the first group by using the CT number corresponding to each of the tissues included in the first group. For example, the first model generating unit 132 may calculate a density of each of the tissues according to Equation 2 below.

$$\rho = 0.00129h^3 - 0.14661h^2 + 5.1286h + 990.34 \quad \text{[Equation 2]}$$

In Equation 2, $\rho$ is a density of a tissue (unit: $kg/m^3$) and h is a CT number of the tissue (unit: HU).

The first model generating unit 132 may calculate a density of each of the tissues of the first group, and approximate the calculated values to generate a model about the density of the tissues included in the first group. A method of generating a model regarding a density by using the first model generating unit 132 may be the same as the method of generating a model regarding a speed of therapeutic ultrasound described above.

Alternatively, the first model generating unit 132 may generate a graph model or a table model regarding attenuation coefficients of therapeutic ultrasound of each of the tissues of the first group by using the CT number corresponding to each of the tissues included in the first group.

The first model generating unit 132 may calculate an attenuation coefficient of therapeutic ultrasound with respect to each of the tissues according to Equation 3 below.

$$\alpha = 0.0000044h^3 - 0.0045h^2 + 0.13h + 0.022 \quad \text{[Equation 3]}$$

In Equation 3, α is an attenuation coefficient of therapeutic ultrasound (unit: db/(MHz*cm)), and h is a CT number of the tissues (unit: HU).

The first model generating unit 132 may calculate an attenuation coefficient of therapeutic ultrasound regarding each of the tissues of the first group, and approximate the calculated values to generate a model about the attenuation coefficient of the tissues included in the first group. A method of generating a model regarding an attenuation coefficient of the tissues included in the first group by using the first model generating unit 132 is the same as the method of generating a model regarding a speed of a therapeutic ultrasound described above.

The first model generating unit 132 transmits the generated information about the first model to the calculation conducting unit 134 (see FIG. 3).

FIG. 5 illustrates a model generated by using a second model generating unit 133 (FIG. 3) according to an embodiment of the present invention.

Referring to FIG. 5, the second model generating unit 133 may generate a second model indicating characteristics of each of the tissues included in the second group. For example, the second model generating unit 133 may generate a table model including a speed of therapeutic ultrasound through each of the tissues, a density of each of the tissues, or an attenuation coefficient of therapeutic ultrasound regarding each of the tissues of the second group (e.g., the bone and fat).

The second model generating unit 133 transmits the generated information about the second model to the calculation conducting unit 134.

Referring to FIG. 1 again, the tissue characteristics calculating unit 130 may output a graph model or a table model generated via the above-described method to the image display device 30 via the interface unit 110.

Referring to FIG. 3 again, the calculation conducting unit 134 calculates characteristics of tissues by using the first model and the second model. In detail, the calculation conducting unit 134 may combine information included in the graph model received from the first model generating unit 132 and information included in the table model received from the second model generating unit 133 to calculate characteristics of tissues existing on a path along which therapeutic ultrasound travels from components of a therapeutic ultrasound probe to foci.

Referring to FIG. 1 again, the calculation conducting unit 134 transmits the information about the calculated characteristics to the parameter calculating unit 140.

The parameter calculating unit 140 calculates one or more parameters of therapeutic ultrasound for forming multi-foci in a region of interest by using the calculated characteristics. In detail, the parameter calculating unit 140 calculates a sound pressure of the therapeutic ultrasound at a position of the therapeutic ultrasound probe by using the calculated characteristics, and calculates a parameter of the therapeutic ultrasound that is to be irradiated from the therapeutic ultrasound probe based on the calculated sound pressure.

The sound pressure refers to a sound pressure calculated at the position of the therapeutic ultrasound elements by assuming positions of multi-foci as virtual sound sources, and a sound source refers to a source that irradiates therapeutic ultrasound. Also, the parameters may include one or more of the following: an amplitude of therapeutic ultrasound and a phase of therapeutic ultrasound.

Figure 6:
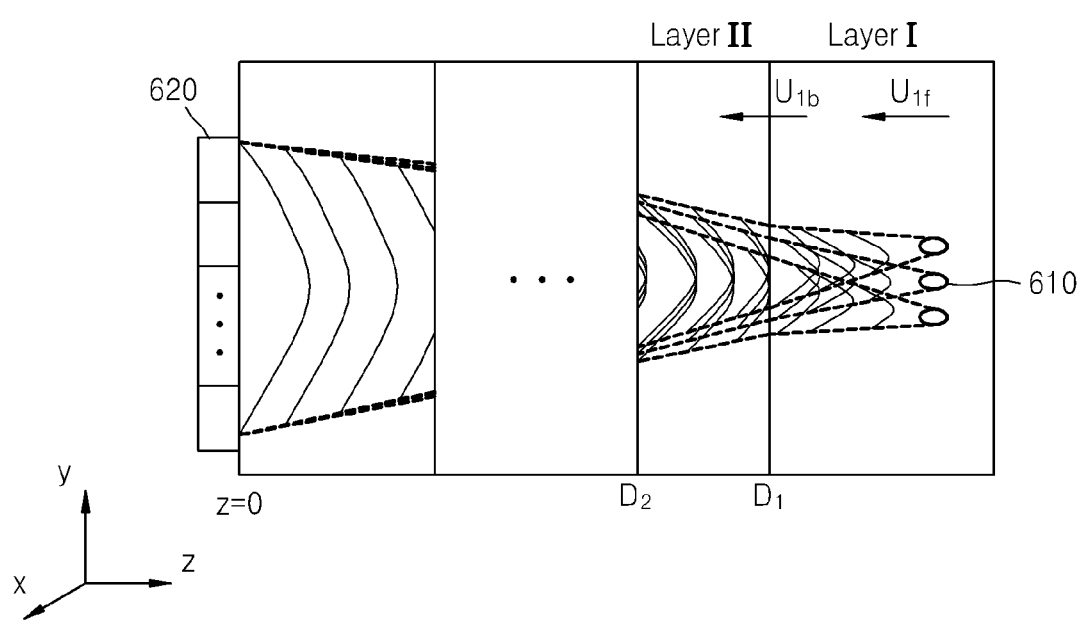
FIG. 6 is a schematic view for explaining an example of a parameter calculating unit that calculates a sound pressure of therapeutic ultrasound at a position of a therapeutic ultrasound probe, according to an embodiment of the present invention.

FIG. 6 is a schematic view for explaining an example of the parameter calculating unit 140 (FIG. 1) calculating a sound pressure of therapeutic ultrasound at a position of a therapeutic ultrasound probe, according to an embodiment of the present invention.

In detail, therapeutic ultrasound irradiated from a therapeutic ultrasound probe 620 forms multi-foci 610 at predetermined positions in a region of interest. Accordingly, a sound pressure of the therapeutic ultrasound is typically calculated at the positions of the multi-foci 610. However, the parameter calculating unit 140 according to the current embodiment of the present invention calculates a sound pressure of the therapeutic ultrasound at a position of the therapeutic ultrasound probe 620 by assuming that the therapeutic ultrasound is irradiated from the multi-foci 610.

In detail, when a plurality of different media (e.g., internal body tissues) are present on a path along which therapeutic ultrasound travels, the parameter calculating unit 140 calculates a transmission sound pressure $U_{1b}$ at which therapeutic ultrasound irradiated from the multi-foci 610 passes through a boundary $D_1$ of the media (i.e., discontinuous boundary) in combination with an incident sound pressure $u1f$ which is incident on the boundary $D_1$, and a transmission coefficient T. Then, the parameter calculating unit 140 applies a two-dimensional Fourier Transform to the transmission sound pressure $U_{1b}$ to calculate an angular spectrum $U_{1b}$ on a plane $D_1$ plane. Then, the parameter calculating unit 140 calculates a sound pressure $U_2$ by calibrating a phase variation due to a distance difference between the plane $D_1$ and a plane $D_2$ based on the sound pressure $U_{1b}$. Thereafter, the parameter calculating unit 140 calculates a sound pressure $U_2$ on the plane $D_2$ by applying an inverse two-dimensional Fourier Transform with respect to the sound pressure $U_2$.

The parameter calculating unit 140 may calculate a sound pressure p of therapeutic ultrasound by repeating the above-described operations according to the number of boundaries existing on the path from the multi-foci 610 to the therapeutic ultrasound probe 620.

However, if the media along the travelling path of the therapeutic ultrasound is not uniform, the method of calculating a sound pressure by using the parameter calculating unit 140 is not limited to the above method using angular spectrum method (ASM), and other methods leading to similar results may be used.

Referring to FIG. 1 again, the parameter calculating unit 140 calculates a parameter of the therapeutic ultrasound to be irradiated from the therapeutic ultrasound probe 20 based on the calculated sound pressure.

As described above, the sound pressure calculated by using the parameter calculating unit 140 refers to a sound pressure calculated by assuming that the multi-foci function as virtual sound sources that irradiate therapeutic ultrasound that travels to the ultrasound treatment irradiating apparatus 20.

Accordingly, the parameter calculating unit 140 may calculate a parameter of therapeutic ultrasound to be irradiated from the therapeutic ultrasound probe 20 by applying a time-reversal method with regard to the calculated sound pressure. As the time-reversal method is obvious to one of ordinary skill in the art, a detailed description thereof will be omitted.

The parameter calculating unit 140 transmits the determined parameter to the ultrasound generating unit 150.

The ultrasound generating unit 150 generates therapeutic ultrasound based on the determined parameter. In detail, the ultrasound generating unit 150 generates information about therapeutic ultrasound that is to be irradiated by using the therapeutic ultrasound probe 20 by using parameters received from the parameter calculating unit 140. Also, the ultrasound generating unit 150 transmits the generated information to the therapeutic ultrasound probe 20.

Figure 7:
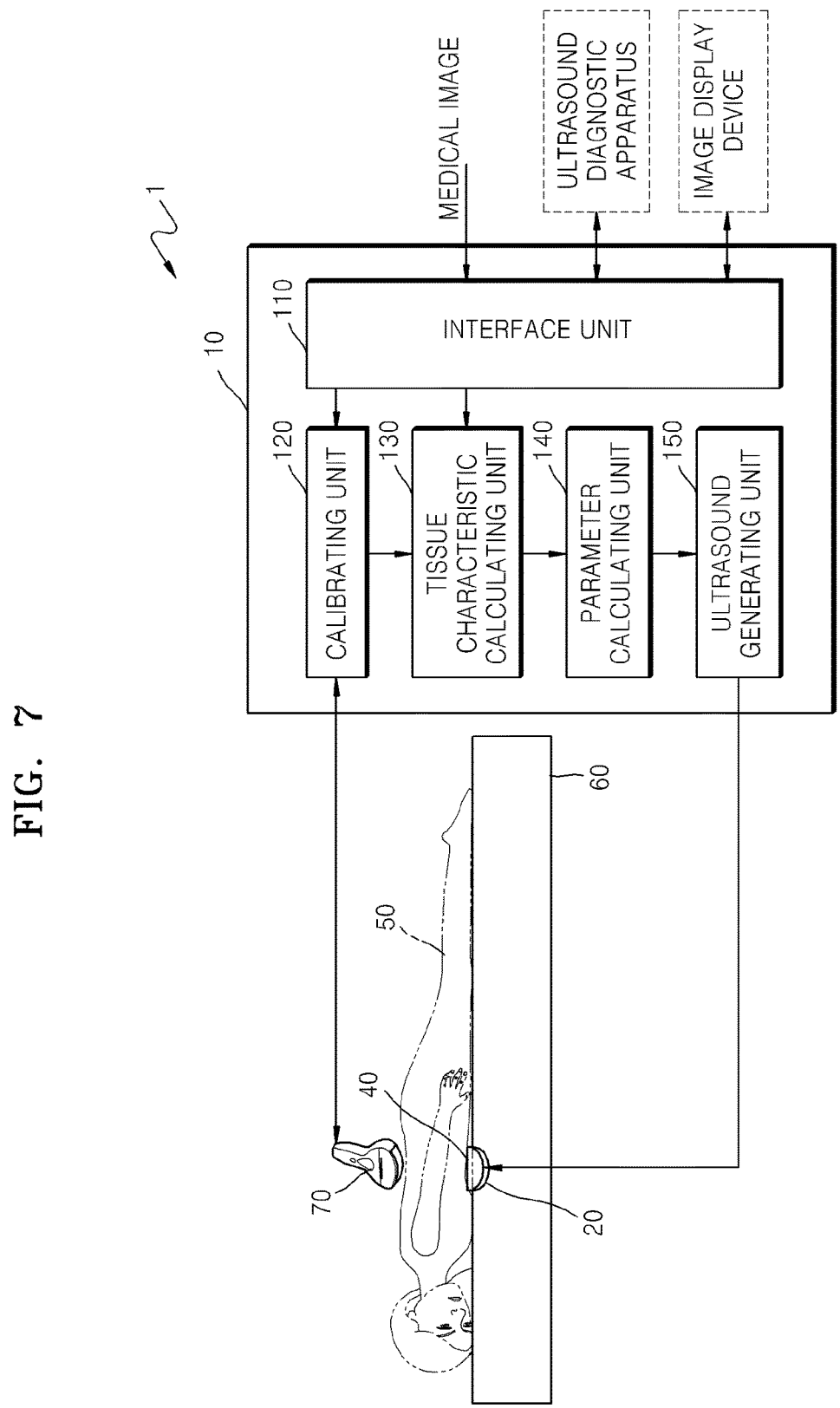
FIG. 7 illustrates a central workstation unit according to another embodiment of the present invention.

FIG. 7 illustrates the central workstation 10 according to another embodiment of the present invention.

Referring to FIG. 7, the central workstation 10 includes an interface unit 110, a tissue characteristics calculating unit 130, a parameter calculating unit 140, an ultrasound generating unit 150, and a calibrating unit 120. Only elements that are related to the current embodiment of the present invention are illustrated in the central workstation 10 of FIG. 8. Thus, it would be obvious to one of ordinary skill in the art that other general-use components other than the elements illustrated in FIG. 7 may be further included in the central workstation 10 of FIG. 8.

Also, the interface unit 110, the tissue characteristics calculating unit 130, the parameter calculating unit 140, and the ultrasound generating unit 150 of the central workstation 10 illustrated in FIG. 7 may include one or a plurality of processors. A processor may be formed as an array including a plurality of logic gates or as a combination of a general-use microprocessor and a memory in which a program that is executable in the microprocessor is stored. Also, it would be obvious to one of ordinary skill in the art that a processor may also include other hardware devices. Also, the interface unit 110, the tissue characteristics calculating unit 130, the parameter calculating unit 140, and the ultrasound generating unit 150 of the central workstation 10 illustrated in FIG. 7 operate in the same manner as described above.

The calibrating unit 120 calibrates the therapeutic ultrasound probe 20 by using a medical image. Calibration refers to calibration of the position or the coordinates of the therapeutic ultrasound probe 20 in order for the therapeutic ultrasound to form multi-foci in a region corresponding to a region of interest in a medical image (for example, a region including a lesion).

Figure 8:
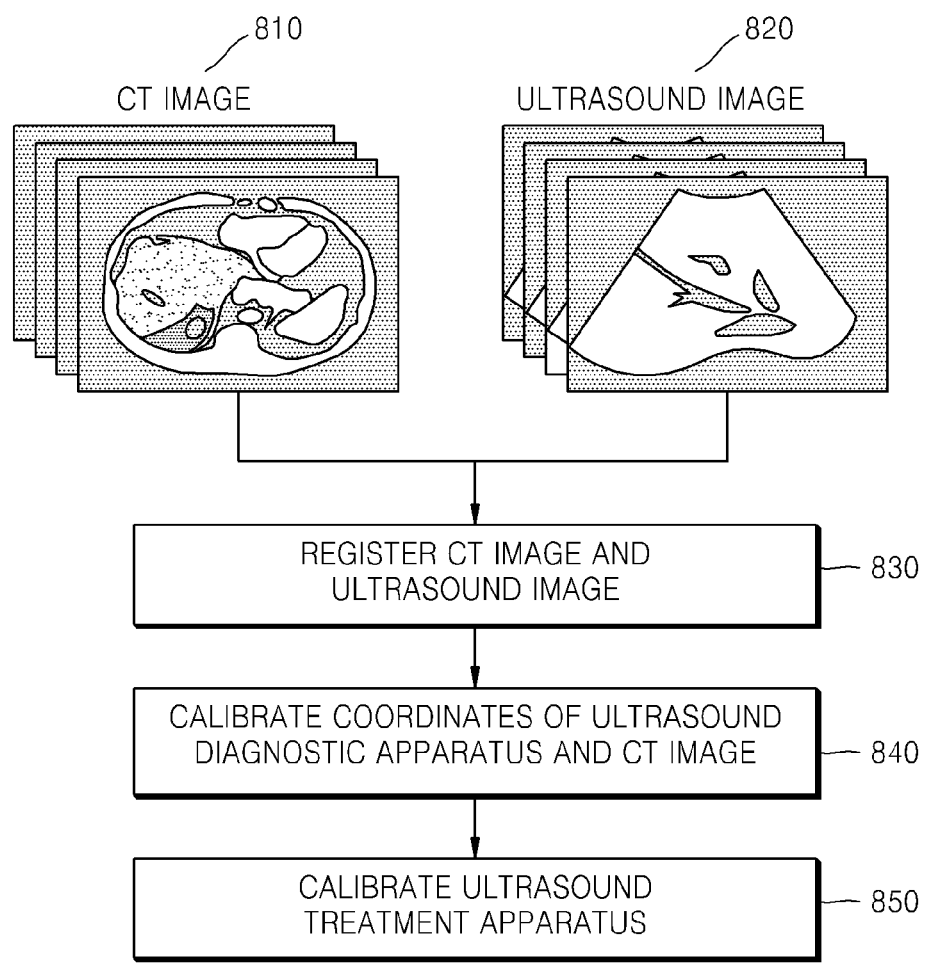
FIG. 8 is a schematic view for explaining an example of a calibrating unit that calibrates a therapeutic ultrasound probe, according to an embodiment of the present invention.

FIG. 8 is a schematic view for explaining an example of the calibrating unit 120 (see FIG. 7) calibrating a therapeutic ultrasound probe, according to an embodiment of the present invention. A medical image will be considered to be a CT image, but the medical image is not limited thereto.

First, the calibrating unit 120 (see FIG. 7) receives electrical pulse signals via the interface unit 110 (see FIG. 7) to generate an ultrasound image 820 regarding a region of interest. However, when a diagnostic ultrasound probe 70 (see FIG. 7) generates an ultrasound image, the calibrating unit 120 obtains the ultrasound image via the interface unit 110.

The calibrating unit 120 registers a medical image 810 received via the interface unit 110 and the ultrasound image 820 regarding a subject in operation 830. The registration refers to an operation of matching a coordinate system on the medical image 810 and a coordinate system on the ultrasound image 820. In detail, the calibrating unit 120 registers the medical image 810 and the ultrasound image 820 by using a geometrical correlative relationship between tissues shown on the medial image 810 and the ultrasound image 820. The geometrical correlative relationship refers to a relationship between landmark points extracted from the tissues.

Then, the calibrating unit 120 calculates a conversion relationship between the coordinate system of the medical image 810 and the coordinate system of the ultrasound image 820 by using a result of registration of the images. For example, the calibrating unit 120 calculates points of the ultrasound image 820 that respectively correspond to points in the medical image 810, and calculates a coordinates conversion matrix needed to match the respective points to each other. The calibrating unit 120 calibrates the diagnostic ultrasound probe 70 by using the calculated coordinates conversion matrix in operation 840.

Then, the calibrating unit 120 calibrates the therapeutic ultrasound probe 20 by using the calibrated diagnostic ultrasound probe 70 in operation 850. The calibration refers to adjusting coordinates of the therapeutic ultrasound probe 20 so that the therapeutic ultrasound probe 20 irradiates therapeutic ultrasound at a point corresponding to a predetermined point (e.g., a lesion) in the medical image 810.

In detail, the diagnostic ultrasound probe 70 and the therapeutic ultrasound probe 20 have a predetermined relative position with respect to each other or may have constant position relationship. Accordingly, the diagnostic ultrasound probe 70 may be calibrated based on the relative positions or the coordinate relationship between the diagnostic ultrasound probe 70 and the therapeutic ultrasound probe 20 in operation 850. The coordinate relationship may be calculated by extension or reduction by using rotation, movement, or a scale factor of a coordinate axis. In detail, a coordinate relationship between a coordinate of a focus formed by diagnostic ultrasound irradiated by the diagnostic ultrasound probe 70 and a coordinate of a focus formed by therapeutic ultrasound irradiated by the therapeutic ultrasound probe 20 may be calculated by extension or reduction by using rotation, movement, or a scale factor of coordinate axes.

Finally, the calibrating unit 120 calculates positions of multi-foci in the medical image 810 as formed by therapeutic ultrasound that is to be irradiated by the therapeutic ultrasound probe 20.

Referring to FIG. 7 again, the calibrating unit 120 transmits information about positions of foci to a control unit (not shown), and the control unit may modify a position where the therapeutic ultrasound probe 20 is to irradiate therapeutic ultrasound according to the calibrated coordinates of the therapeutic ultrasound probe 20.

In addition, the calibrating unit 120 may transmit information about positions of foci to the tissue characteristics calculating unit 130, and the tissue characteristics calculating unit 130 may detect a path along which therapeutic ultrasound is to travel based on the received information.

Thus, as the calibrating unit 150 calibrates the therapeutic ultrasound probe 20, the therapeutic ultrasound probe 20 may accurately irradiate therapeutic ultrasound toward the multi-foci.

Figure 9:
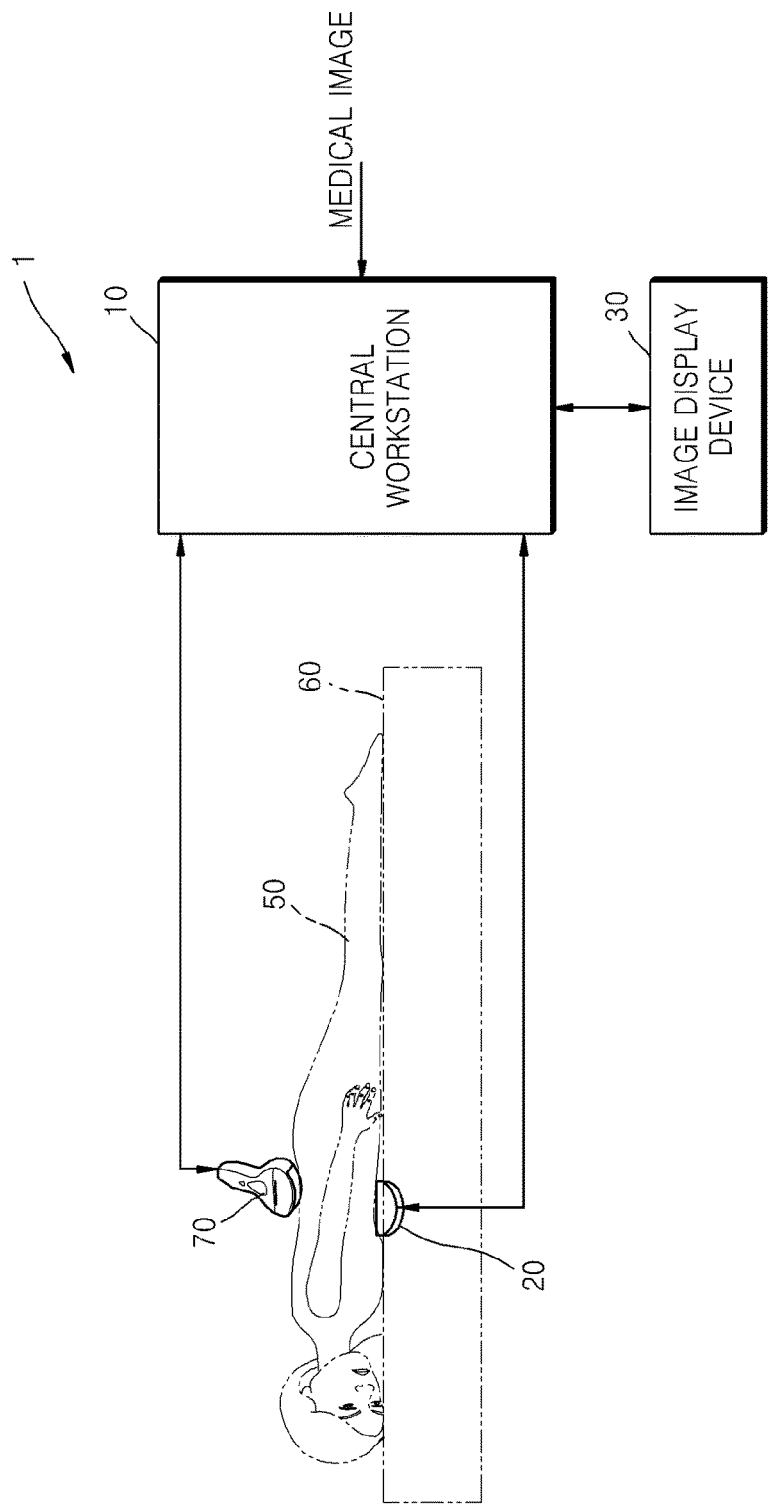
FIG. 9 illustrates a HIFU system according to another embodiment of the present invention.

FIG. 9 illustrates a HIFU system 1 according to another embodiment of the present invention.

The HIFU system 1 according to the current embodiment of the present invention includes a central workstation 10 and a therapeutic ultrasound probe 20. The HIFU system 1 may further include an image display device 30 or a diagnostic ultrasound probe 70.

In FIG. 9, only elements related to the current embodiment of the present invention are illustrated in the HIFU system 1. Accordingly, it would be obvious to one of ordinary skill in the art that other general-use components may be further included in the HIFU system 1.

Also, the HIFU system 1 illustrated in FIG. 9 corresponds to an embodiment of the central workstations 10 illustrated in FIGS. 1 and 7. Thus, the description provided in regard to FIGS. 1 and 7 may also apply to the HIFU system 1 illustrated in FIG. 9.

The diagnostic ultrasound probe 70 irradiates diagnostic ultrasound to a region of interest of a subject 50, and obtains a reflected ultrasound signal. In detail, the diagnostic ultrasound is partially reflected at layers between various tissues of the region of interest. The reflected ultrasound signal vibrates a piezoelectric transducer of the diagnostic ultrasound probe 70, and thus, the piezoelectric transducer outputs electrical pulses according to the vibration.

However, the diagnostic ultrasound probe 70 may immediately generate an ultrasound image regarding a region of interest by using the electrical pulse signals, or the central workstation 10 may generate an ultrasound image about a region of interest by using the electrical pulse signals. When the diagnostic ultrasound probe 70 directly generates an ultrasound image, the diagnostic ultrasound probe 70 transmits information about the generated ultrasound image, to the central workstation 10. Meanwhile, when the central workstation 10 generates an ultrasound image, the diagnostic ultrasound probe 70 transmits the electrical pulse signals to the central workstation 10.

Also, the diagnostic ultrasound probe 70 and the therapeutic ultrasound probe 20 have a constant position relationship. For example, the diagnostic ultrasound probe 70 and the therapeutic ultrasound probe 20 may operate while being separated a predetermined distance from each other or while being adjacent to each other.

Meanwhile, while the therapeutic ultrasound probe 20 is illustrated as being positioned in the bed 60 in FIGS. 1, 7, and 9, the embodiments of the present invention are not limited thereto. For example, the therapeutic ultrasound probe 20 may be located above the subject 50 to irradiate therapeutic ultrasound downward.

The image display device 30 displays an ultrasound image generated by using the central workstation 10. For example, the image display device 30 includes any of output devices provided in the HIFU system 1 such as a display panel, a liquid crystal display (LCD) screen, or a monitor. Information about a region of interest obtained by using the central workstation 10 may be provided to the user by using the image display device 30 and be used in detecting a state of a tissue or a variation in a position or a shape of a tissue.

Figure 10:
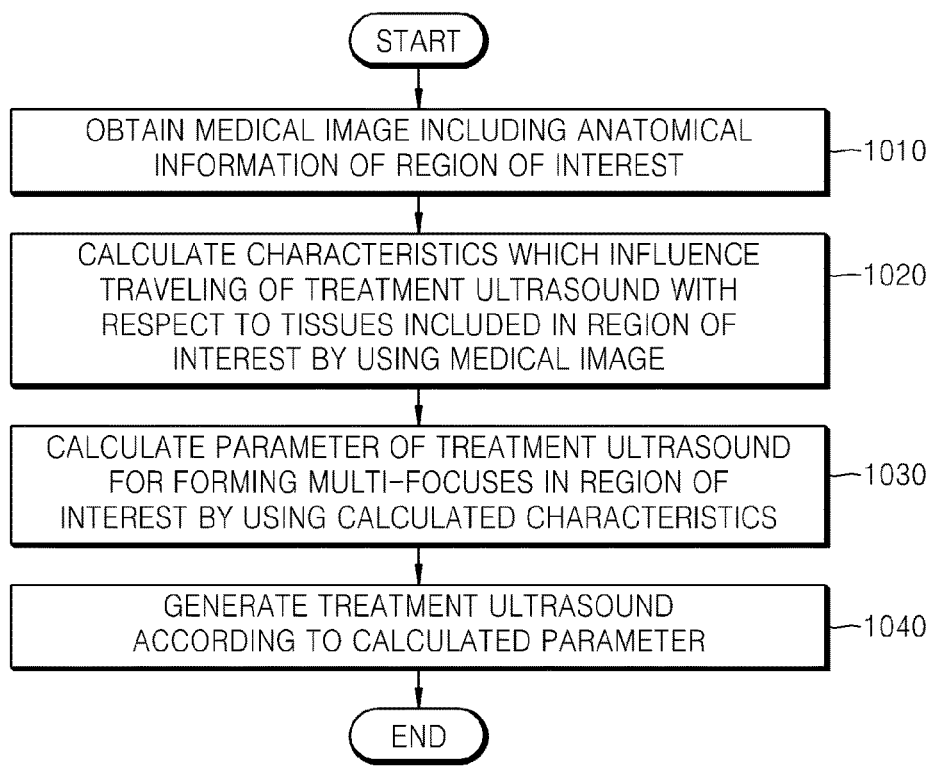
FIG. 10 is a flowchart illustrating a method of generating ultrasound that forms multi-foci in a region of interest, the method being performed by using a central workstation according to an embodiment of the present invention.

FIG. 10 is a flowchart illustrating a method of generating ultrasound that forms multi-foci in a region of interest, the method being performed by using the central workstation 10 according to an embodiment of the present invention.

Referring to FIG. 10, the method of generating ultrasound includes operations that may be time-sequentially performed in the central workstation 10 or the HIFU system 1 illustrated in FIGS. 1, 7, and 9. Accordingly, the descriptions which are omitted below but have been provided with regard to the central workstations 10 illustrated in FIGS. 1, 7, and 9 above may also apply to the method of generating an ultrasound illustrated in FIG. 10.

In operation 1010, a medical image including anatomical information about a region of interest is obtained via the interface unit 110.

In operation 1020, the tissue characteristics calculating unit 130 calculates, by using the obtained medical image, characteristics of tissues included in a region of interest and which may influence traveling of therapeutic ultrasound.

In operation 1030, the parameter calculating unit 140 calculates a parameter of therapeutic ultrasound for forming multi-foci in a region of interest by using the calculated characteristics.

In operation 1040, the ultrasound generating unit 150 generates therapeutic ultrasound according to the calculated parameter.

According to the embodiments of the present invention described above, therapeutic ultrasound generated by using the central workstation 10 forms multi-foci in a region of interest, thereby reducing the time needed for treating a lesion that is distributed over a wide area. In addition, the central workstation 10 accurately calculates positions of the multi-foci formed by the therapeutic ultrasound and the amplitude and phase of the therapeutic ultrasound, and thus, safety of the HIFU treatment may be improved.

According to the embodiments of the present invention, the treatment time of a lesion that is distributed over a wide area may be reduced by forming multi-foci in a region of interest. Also, by accurately calculating positions of multi-foci formed by therapeutic ultrasound and the amplitude and phase of the therapeutic ultrasound, the safety of the HIFU treatment may be improved.

In addition, data structures used in the above-described method may be recorded on a non-transitory computer readable recording medium in various manners. Examples of the non-transitory computer readable recording medium may include magnetic storage media (e.g., ROM, RAM, USB, floppy disks, hard disks, etc.), optical recording media (e.g., CD-ROM, DVD, etc.), and storage media such as PC interface (e.g., PCI, PCI-express, WiFi, etc.).

It should be understood that the exemplary embodiments described therein should be considered in a descriptive sense only and not for purposes of limitation. Descriptions of features or aspects within each embodiment should typically be considered as available for other similar features or aspects in other embodiments.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A method of generating therapeutic ultrasound that forms multi-foci by using a therapeutic ultrasound probe, the method comprising:

obtaining a medical image comprising anatomical information of tissues in a region of interest in a body;

calculating, by using the medical image, characteristics of the tissues in the region of interest;

calculating, with respect to virtual sound sources at positions of the multi-foci, a sound pressure of assumed therapeutic ultrasound at a position of the therapeutic ultrasound probe based on the calculated characteristics of the tissues in the region of interest;

calculating, by using the calculated sound pressure, one or more parameters of the assumed therapeutic ultrasound; and generating final therapeutic ultrasound according to the calculated one or more parameters, wherein the generated final therapeutic ultrasound, when irradiated on the region of interest, forms the multi-foci in the region of interest.

2. The method of claim 1, wherein the calculating, with respect to the virtual sound sources at the positions of the multi-foci, the sound pressure of the assumed therapeutic ultrasound comprises calculating the sound pressure of the assumed therapeutic ultrasound at the position of the therapeutic ultrasound probe based on an assumption that the assumed therapeutic ultrasound is irradiated by the virtual sound sources at the positions of the multi-foci.

3. The method of claim 1, wherein the calculating of the characteristics of the tissues in the region of interest comprises:

calculating, by using the medical image, the characteristics of the tissues in the region of interest for each of a plurality of tissues in the region of interest that are present on paths of the assumed therapeutic ultrasound from elements of the therapeutic ultrasound probe to the multi-foci.

4. The method of claim 1, wherein the calculated characteristics of the tissues comprise one or more of:
a speed of the assumed therapeutic ultrasound through each of the tissues,
a density of each of the tissues, and
an attenuation coefficient of the assumed therapeutic ultrasound regarding each of the tissues.

5. The method of claim 1, further comprising:
calibrating the therapeutic ultrasound probe by using the medical image,
wherein the calculating of the characteristics of the tissues in the region of interest comprises:
calculating the characteristics of the tissues in the region of interest for each of a plurality of tissues in the region of interest being present on paths of the assumed therapeutic ultrasound from elements of the therapeutic ultrasound probe to the multi-foci by using the calibrated therapeutic ultrasound probe and the medical image.

6. The method of claim 5, wherein the calibrating comprises:
generating an ultrasound image of the region of interest by using a diagnostic ultrasound probe;
calibrating the diagnostic ultrasound probe by using an image obtained by registering the ultrasound image and the medical image; and
calibrating the therapeutic ultrasound probe by using calibration information of the diagnostic ultrasound probe.

7. The method of claim 1, wherein the medical image is a tomography (CT) image.

8. The method of claim 7, wherein the calculating of the characteristics of the tissues in the region of interest is performed for each of the tissues in the region of interest, and the characteristics of the tissues in the region of interest which influence traveling of the assumed therapeutic ultrasound, and
wherein the calculating of the characteristics of the tissues in the region of interest for each of the tissues comprises:
grouping the tissues of the region of interest into a first group and a second group according to a CT number of each of the tissues in the region of interest obtained from the medical image;
generating a first model representing the characteristics with respect to each of the tissues in the region of interest grouped in the first group;
generating a second model representing the characteristics with respect to each of the tissues in the region of interest grouped in the second group; and
calculating the characteristics of the tissues in the region of interest for each of the tissues grouped in the first group and the second group by using the first model and the second model, respectively.

9. The method of claim 1, wherein the calculated one or more parameters of the assumed therapeutic ultrasound comprise at least one of: an amplitude, and a phase of the assumed therapeutic ultrasound.

10. A non-transitory computer readable storage medium having stored thereon a program, which, when executed by a computer, causes the computer to perform:

obtaining a medical image comprising anatomical information of tissues in a region of interest in a body;
calculating, by using the medical image, characteristics of the tissues in the region of interest which influence traveling of assumed therapeutic ultrasound;
calculating, with respect to virtual sound sources at positions of multi-foci, a sound pressure of the assumed therapeutic ultrasound at a position of a therapeutic ultrasound probe based on the calculated characteristics of the tissues in the region of interest;
calculating, by using the calculated sound pressure, one or more parameters of the assumed therapeutic ultrasound; and
generating final therapeutic ultrasound according to the calculated one or more parameters;
wherein the generated final therapeutic ultrasound, when irradiated on the region of interest, forms the multi-foci in the region of interest.

11. A therapeutic ultrasound system for generating therapeutic ultrasound forming multi-foci, the therapeutic ultrasound system comprising:
a processor configured to execute instructions to:
calculate, by using a medical image comprising anatomical information of tissues in a region of interest, characteristics of the tissues in the region of interest which influence traveling of assumed therapeutic ultrasound;
calculate, with respect to virtual sound sources at positions of the multi-foci, a sound pressure of the assumed therapeutic ultrasound at a position of a therapeutic ultrasound probe based on the calculated characteristics of the tissues in the region of interest;
calculate, by using the calculated sound pressure, one or more parameters of the assumed therapeutic ultrasound; and
generate final therapeutic ultrasound according to the calculated one or more parameters;
wherein the generated final therapeutic ultrasound, when irradiated on the region of interest, forms the multi-foci in the region of interest.

12. The therapeutic ultrasound system of claim 11, wherein the sound pressure is calculated at the position of the therapeutic ultrasound probe based on an assumption that the assumed therapeutic ultrasound is irradiated by the virtual sound sources at the positions of the multi-foci.

13. The therapeutic ultrasound system of claim 11, wherein the processor calculates, by using the medical image, the characteristics of the tissues in the region of interest for each of a plurality of tissues in the region of interest that are present on paths of the assumed therapeutic ultrasound from elements included in the therapeutic ultrasound probe to the multi-foci.

14. The therapeutic ultrasound system of claim 11, wherein the processor calibrates the therapeutic ultrasound probe by using the medical image,
wherein the processor calculates the characteristics of the tissues in the region of interest for each of a plurality of tissues in the region of interest that are present on paths of the assumed therapeutic ultrasound by using the calibrated therapeutic ultrasound probe and the medical image.

15. The therapeutic ultrasound system of claim 14, wherein the processor generates an ultrasound image with respect to the region of interest by using a diagnostic ultrasound probe, calibrates the diagnostic ultrasound probe by using an image obtained by registering the ultrasound image and the medical image, and calibrates the therapeutic ultrasound probe by using calibration information of the diagnostic ultrasound probe.

16. The therapeutic ultrasound system of claim 11, wherein the medical image is a computed tomography (CT) image.

17. The therapeutic ultrasound system of claim 11, wherein the processor further executes instructions to:
- group the tissues of the region of interest into a first group and a second group by using a CT number, of each of the tissues of the region of interest, obtained from the medical image;
- generate a first model representing the characteristics of each of the tissues in the region of interest grouped in the first group;
- generate a second model representing the characteristics of the tissues in the region of interest grouped in the second group; and
- calculate the characteristics of the tissues in the region of interest grouped in the first group and the second group by using the first model and the second model, respectively.

* * * * *